(12) United States Patent
Bardou

(10) Patent No.: US 9,161,925 B2
(45) Date of Patent: Oct. 20, 2015

(54) THERAPEUTIC USES OF BETA-3 ADRENERGIC RECEPTOR AGONIST DERIVATIVES IN PARTICULAR TO MODULATE APOPTOSIS

(75) Inventor: Marc Bardou, Dijion (FR)

(73) Assignee: SANOFI, Paris (FR)

( * ) Notice: Subject to any disclaimer, the term of this patent is extended or adjusted under 35 U.S.C. 154(b) by 242 days.

(21) Appl. No.: 12/652,317

(22) Filed: Jan. 5, 2010

(65) Prior Publication Data

US 2010/0311829 A1 Dec. 9, 2010

Related U.S. Application Data

(63) Continuation of application No. PCT/IB2008/002752, filed on Jul. 4, 2008.

(30) Foreign Application Priority Data

Jul. 5, 2007 (EP) .................................. 07290845

(51) Int. Cl.
*A61K 31/24* (2006.01)
*A61K 31/18* (2006.01)

(52) U.S. Cl.
CPC .................................... *A61K 31/18* (2013.01)

(58) Field of Classification Search
None
See application file for complete search history.

(56) References Cited

FOREIGN PATENT DOCUMENTS

| WO | WO 0244139 | 6/2002 |
|---|---|---|
| WO | WO 03099772 | 4/2003 |
| WO | WO 03099819 | 4/2003 |

OTHER PUBLICATIONS

Olgun et al (Obstetrics and Gynecology Int 2010:1-8, 2010).*
Croci et al (J Pharmacol Exp Ther 321:1118-1126, published Mar. 9, 2007).*
Ngassa et al (Int J Gynaecol Obstet 47:241-246, 1994 (Abstract only)).*
Perfettini et al (Infection and Immunity 68:2237-2244, 2000).*
Tiziano Crocl et al., In Vitro and in Vivo Pharma. Characterization of Ethyl-4-{trans-4[((2S)-2-hydroxy-3-(4-hydroxy-3[(methylsulfonyl)amino]-phenoxy)propyl) Amino]cyclohexy)benzoate Hydrochloride (SAR 150640), a New Potent and Selective Human Beta3-Adrenoceptor Agonist for the Treatment of Preterm Labor, The J.I of Pharm. and Experimental Therapeutics (2007), pp. 1110-1126, vol. 321.
Elaine DiFederico et al., Preeclampsia is Associated with Widespread Apoptosis of Placental Cytotrophoblasts within the Uterine Wall, American Journal of Pathology, (1999) pp. 293-301, vol. 155, No. 1.
M. Fuerst, "[beta]-Blockers may have role in preeclampsia", Journal of the American Medical Association, (1982), pp. 518-513, vol. 248, No. 5.
S. Katooka et al., Increased Apoptosis of Human Fetal Membranes in Rupture of the Membranes and Chorioamnionitis, Placenta, (2002), pp. 224-231, vol. 23.
D. L. Rivera et al., Interkeukin-10 attenuates experimental fetal growth restriction and demise, FASEB Journal, (1998) pp. 198-197, vol. 12, No. 2.

* cited by examiner

*Primary Examiner* — Craig Ricci
(74) *Attorney, Agent, or Firm* — Morrison & Foerster LLP

(57) ABSTRACT

The present invention relates to the new therapeutic uses of beta-3 adrenergic receptor agonist derivatives in particular to inhibit apoptosis and treat and/or prevent apoptosis-related diseases and disorders.

12 Claims, 3 Drawing Sheets ized as tocolytic agents (Kim et al., *Bjog* 113 *Suppl* 3:113-115, 2006). It has recently been shown that ADRB3 is present, and is the predominant ADRB, in human myometrium (Bardou et al., *Br J Pharmacol* 130:1960-1966, 2000; Dennedy et al., *Bjog* 108:605-609, 2001; Rouget et al., *J Clin Endocrinol Metab* 90:1644-1650, 2005) with an inhibitory action on spontaneous contractions.

SEQUENCE LISTING

```
<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
tgcaccacca actgcttagc                                               20

<210> SEQ ID NO 2
<211> LENGTH: 21
<212> TYPE: DNA
<213> ORGANISM: Homo sapiens

<400> SEQUENCE: 2
ggcatggact gtggtcatga g                                             21

<210> SEQ ID NO 3
<211> LENGTH: 22
<212> TYPE: DNA
<213> ORGANISM: Homo sapiens

<400> SEQUENCE: 3
agaactggac tgtggcattg ag                                            22

<210> SEQ ID NO 4
<211> LENGTH: 22
<212> TYPE: DNA
<213> ORGANISM: Homo sapiens

<400> SEQUENCE: 4
gcttgtcggc atactgtttc ag                                            22
```

THERAPEUTIC USES OF BETA-3 ADRENERGIC RECEPTOR AGONIST DERIVATIVES IN PARTICULAR TO MODULATE APOPTOSIS

The present invention relates to the novel therapeutic uses of beta-3 adrenergic receptor agonist derivatives in particular to modulate apoptosis.

Beta-2-adrenergic receptor (ADRB2) agonists have long been used as tocolytic agents for the treatment of preterm labor, but, due to limited efficacy and toxicity, are no longer recommended as first choice drugs. Oxytocin antagonists and calcium channel blockers are more recently developed drugs with a lower profile of adverse affects, and hence more commonly used, even if calcium channel blockers, which were developed to treat hypertension, including in pregnant women, are not approved as tocolytic agents (Kim et al., *Bjog* 113 *Suppl* 3:113-115, 2006). It has recently been shown that ADRB3 is present, and is the predominant ADRB, in human myometrium (Bardou et al., *Br J Pharmacol* 130:1960-1966, 2000; Dennedy et al., *Bjog* 108:605-609, 2001; Rouget et al., *J Clin Endocrinol Metab* 90:1644-1650, 2005) with an inhibitory action on spontaneous contractions.

Apoptosis is one of the main types of programmed cell death (PCD), and involves an orchestrated series of biochemical events leading to a characteristic cell morphology and death. Research on apoptosis has increased substantially since the early 1990s. In addition to its importance as a biological phenomenon, defective apoptotic processes have been implicated in an extensive variety of diseases. Cancer is a prime example of the crucial role of apoptotic regulation as defective anti-apoptotic effectors may result in uncontrolled cell proliferation.

The review by Solary et al., *Eur. Respir. J.* 9, 1293-1305, 1996 confirms the role of apoptosis in cancers; viral infections; autoimmune diseases, such as systemic lupus erythematosus (SLE), rheumatoid arthritis, autoimmune diabetes mellitus, inflammatory bowel syndrome, type 1 diabetes mellitus; fas-mediated disease such as fulminent hepatitis, CTL-mediated autoimmune disease including chronic thyroiditis; AIDS; haematological diseases such as myelodisplastic syndromes, aplastic anaemia, chronic neutropenia, severe beta-thalassaemia; neurodegenerative disorders such as Alzheimer's disease, Parkinson's disease, cerebellar degeneration, retinal pigmentosa, spinal muscular atrophy; and other various diseases including polycystic kidney disease, toxic-induced liver diseases, ischaemic injury, such as myocardial infarction or stroke, atheroma, arthritis, osteoporosis and ageing.

Apoptosis is also largely involved in uterine cell turnover and early pregnancy. It is well-documented that the rodent uterine epithelium around the embryo undergoes apoptosis in response to the presence of the blastocyst (Schlafke et al., *Anat. Rec.* 212:47-56, 1985; Parr et al., *Biol. Reprod.* 36:211-225, 1987; and Welsh et al., *Am. J. Anat.* 192:215-231, 1991). Joswig et al., *Reproductive Biology and Endocrinology* 1:44, 2003, proposed two different pathways for apoptosis in uterine epithelium and decidua in response to implantation. More recently, Qian Zhang et al., *Endocrinology* 147(5), 2215-2227, 2006, studied apoptosis and proliferation in uterine cell turnover during the estrous cycle and early pregnancy. Their results indicate that uterine cell apoptosis and proliferation patterns are highly ordered cell-specific phenomena that play an important role in maintaining the sexual cycle and pregnancy-associated uterine changes. In particular, they indicate that caspase-3-mediated cell apoptosis may play an important role in initiating the implantation process in hamsters and mice.

The first topic of interest for apoptosis in the field of pregnancy is the pathologies of the placenta. Indeed apoptosis of villous trophoblast is upregulated in both of the common pregnancy diseases related to the placenta, namely, intrauterine growth restriction (IUGR) and preeclampsia (Smith S C, et al. Am J Obstet Gynecol 1997; 177:1395-401; Allaire A D et al. Obstet Gynecol 2000; 96:271-6; Erel C T et al. Int J Gynaecol Obstet 2001; 73:229-35; Ishihara N, et al. Am J Obstet Gynecol 2002; 186:158-66.). Since it has recently been shown that apoptotic nuclei are more abundant in fetal growth restricted placentas compared with control placentas (Madazli R, et al. J Obstet Gynaecol 2006; 26:5-10) inhibiting apoptosis can be considered as promising approach to treat or prevent IUGR or preeclampsia.

Spontaneous preterm labor, whether explained or unexplained, is one of the largest causes of preterm birth which in turn is the most frequent cause of infant death in the United States (Callaghan et al., *Pediatrics* 118, 1566-1573, 2006). Many cases of spontaneous preterm labor are unexplained but a significant proportion is linked to genital tract infection or chorioamnionitis (Edwards et al., *Obstet. Gynecol. Clin. North Am.* 32, 287-296, 2005).

Charpigny et al., *Biol. Reprod.*, 68, 2289-2296, 2003, showed that apoptosis associated genes were up-regulated during parturition.

Apoptotic cell death can be initiated by two alternative convergent pathways: the extrinsic pathway, which is mediated by cell surface death receptors, and the intrinsic pathway, which is mediated by mitochondria (Danial et al., *Cell* 116:205-219, 2004). In both pathways, cysteine aspartyl-specific proteases (caspases) which cleave cellular substrates are activated, and activation of the effector caspase-3 is important for the execution of apoptotic cell death. The bcl2 family members play a central role in the regulation of apoptosis. The multidomain proapoptotic proteins Bax and Bak together constitute a requisite gateway to apoptotic cell death because cells doubly deficient for these proteins are resistant to several different intrinsic death stimuli (Danial et al., *Cell* 116:205-219, 2004). Therefore BAX, Bcl-2 and cleaved caspase-3 are widely used to assess apoptosis.

WO02/44139 discloses that certain propanolamines bearing a cyclohexyl(alkyl) group on the amine possess a powerful agonist activity with respect to ADRB3. This document suggests that these compounds may be indicated in the treatment of gastrointestinal diseases such as inflammatory diseases of the intestine, for instance irritable bowel disease (IBD), as modulators of intestinal motivity, as lipolytic agents, anti-obesity agents, anti-diabetic agents, psychotropic agents, anti-glaucoma agents, cicatrizing agents and antidepressants, as inhibitors of uterine contractions, as tocolytics for preventing or delaying preterm births, and for the treatment and/or prophylaxis of dysmenorrhoea. In addition, these compounds could be used in the treatment of certain diseases of the central nervous system, such as for example depression, and also of certain disorders of the urinary system, such as urinary incontinence.

Nevertheless, the use of these compounds for preventing and/or inhibiting apoptosis is neither disclosed nor suggested. More generally the nexus between ADRB3 and apoptosis has not been established or suggested so far.

There is therefore a need to identify new biological targets for controlling apoptosis and modulators thereof.

The present inventors have now found, and that is an object of the present invention, that ADRB3 plays a crucial role in controlling apoptotic pathways, in particular in pregnancy related tissues, namely uterus, placenta and fetal membranes. Additionally, it has also been surprisingly discovered that compounds disclosed in WO02/44139 are potent apoptosis inhibitors.

According to a first object, the present invention concerns the use of a beta-3 adrenergic receptor agonist for the preparation of a medicament for preventing pregnancy related tissues apoptosis in female mammalian patients.

According to another object, the present invention concerns the use of a beta-3 adrenergic receptor agonist for the preparation of a medicament suitable to prevent and/or treat pregnancy related tissues apoptosis related diseases and/or disorders; more particularly to prevent and/or treat uterine apoptosis related diseases and/or disorders; more particularly to prevent and/or treat pregnancy related tissues apoptosis related diseases and/or disorders selected from sexual cycle disorders, fertility disorders and pregnancy disorders.

According to another object, the present invention concerns the use of a beta-3 adrenergic receptor agonist for the preparation of a medicament suitable to prevent and/or treat pregnancy related tissues apoptosis related diseases and/or disorders in female mammalian patients suffering from genital tract infection; more particularly to prevent and/or treat preterm labor in female mammalian patients suffering from genital tract infection; more particularly to prevent and/or treat preterm labor in female mammalian patients suffering from genital tract infection wherein genital tract infection is chorioamnionitis.

According to another object, the present invention concerns the use of a beta-3 adrenergic receptor agonist for the preparation of a medicament suitable to prevent and/or inhibit pregnancy related tissues apoptosis in pregnant women.

According to another object, the present invention concerns the use of a beta-3 adrenergic receptor agonist for the preparation of a medicament for preventing uterine apoptosis in women suffering from genital tract infection, with its consequences mainly preterm labor and preterm delivery.

According to another object, the present invention concerns the use of a beta-3 adrenergic receptor agonist for the preparation of a medicament suitable to prevent and/or treat fetal membranes apoptosis in women suffering from preterm premature rupture of fetal membranes.

According to another object, the present invention concerns the use of a beta-3 adrenergic receptor agonist for the preparation of a medicament suitable to prevent and/or treat placental apoptosis in women with pregnancy complicated by intrauterine growth restriction or preeclampsia.

According to another object, said beta-3 adrenergic receptor agonist is selected from compounds of formula (I):

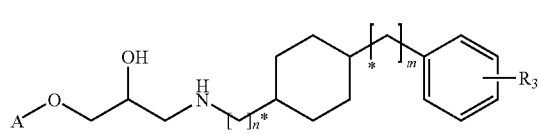

(I)

where in formula (I):
A is a group of formula (a) or (b):

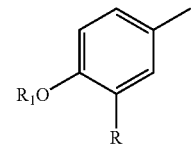

(a)

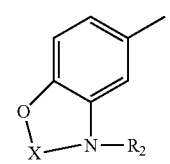

(b)

where:
R represents a hydrogen or halogen atom, an —S(O)$_z$(C$_1$-C$_4$)alkyl group, an —NHSO$_2$(C$_1$-C$_4$)alkyl group, an —SO$_2$NH(C$_1$-C$_4$)alkyl group, an —NHSO$_2$-phenyl-(C$_1$-C$_4$) alkyl group or an —NHSO$_2$-phenyl group, said phenyl possibly being substituted with a halogen atom, with a (C$_1$-C$_4$) alkyl group or with a (C$_1$-C$_4$)alkoxy group;

R$_1$ represents a hydrogen atom or a (C$_1$-C$_4$)alkyl group, a —CO(C$_1$-C$_4$)alkyl group, a phenyl-(C$_1$-C$_4$)alkyl group or a —CO-phenyl group, said phenyl possibly being substituted with a halogen atom or with a (C$_1$-C$_4$)alkoxy group;

R$_2$ is a hydrogen atom, an —SO$_2$(C$_1$-C$_4$)alkyl group, an —SO$_2$-phenyl-(C$_1$-C$_4$)alkyl group or an —SO$_2$-phenyl group;

X completes a ring of 5 to 8 atoms, said ring being saturated or unsaturated, possibly being substituted with one or two (C$_1$-C$_4$)alkyl groups and bearing one or two carbonyl groups;

n, m and z are, independently, 0, 1 or 2;

R3 represents a hydrogen or halogen atom, a (C$_1$-C$_6$)alkyl group, a (C$_1$-C$_4$)alkoxy group, a —COO(C$_1$-C$_4$)alkyl group, a —CO(C$_1$-C$_4$)alkyl group, an —NHSO$_2$(C$_1$-C$_4$)alkyl group, an —NHSO$_2$-phenyl-(C$_1$-C$_4$)alkyl group, —NO$_2$, —CN, —CONR$_4$R$_5$, —COOH, or a 4,5-dihydro-1,3-oxazol-2-yl or 4,4-dimethyl-4,5-dihydro-1,3-oxazol-2-yl group;

R$_4$ and R$_5$ represent, independently, a hydrogen atom, a phenyl, a (C$_1$-C$_4$)alkyl group or a phenyl-(C$_1$-C$_4$)alkyl group; or R$_4$ and R$_5$ with the nitrogen atom to which they are attached, may form a ring of 5 to 7 atoms in total;
and the salts thereof.

In the present description, the terms "(C$_1$-C$_4$)alkyl" and "(C$_1$-C$_6$)alkyl" denote monovalent radicals formed from a respectively C$_1$-C$_4$ and C$_1$-C$_6$ hydrocarbon containing a straight or branched saturated chain.

In the present description, the term "halogen" denotes an atom chosen from chlorine, bromine, iodine and fluorine.

More particularly compounds are those in which n and m are each zero.

More particularly compounds are those in which R$_1$ is a hydrogen atom.

More particularly compounds are those in which R is chosen from an —NHSO$_2$(C$_1$-C$_4$)alkyl group, an —NHSO$_2$-phenyl-(C$_1$-C$_4$)alkyl group or an —NHSO$_2$-phenyl group.

More particularly compounds are those in which R$_3$ is —COO(C$_1$-C$_4$)alkyl or —CO(C$_1$-C$_4$)alkyl or CONR$_4$R$_5$.

More particularly compounds are those in which R$_3$ is in position 4 of the benzene.

More particularly compounds are those in which z is 2.

More particularly compounds are those in which X is a methylene, an ethylene or a propylene.

More particularly compounds are those in which X is a carbonyl, a —CO—CO-group, a —CO—C(($C_1$-$C_4$)alkyl)$_2$-CO— group, a methylene monosubstituted or disubstituted with ($C_1$-$C_4$)alkyl or a —COCH$_2$— group.

More particularly —NHSO$_2$-phenyl-($C_1$-$C_4$)alkyl and —SO$_2$-phenyl-($C_1$-$C_4$)alkyl groups are, respectively, benzylsulphonylamino and benzylsulphonyl.

When $R_4$ and $R_5$ form, with the nitrogen atom to which they are attached, a ring of 5 to 7 atoms, rings more particularly are piperidine and pyrrolidine.

The following compound is particularly advantageous:

Ethyl-4-{trans-4-[((2S)-2-hydroxy-3-{4-hydroxy-3[(methylsulfonyl)-amino]phenoxy}propyl)amino] cyclohexyl}benzoate hydrochloride, herein called Compound A; it is a compound of formula (I) as disclosed above where A is a group of formula (a) where R is —NHSO$_2$-Methyle, $R_1$ is OH, n=m=0 and $R_3$ is —COOEthyle.

The salts of the compounds of formula (I) according to the present invention comprise both the addition salts with pharmaceutically acceptable inorganic or organic acids, such as hydrochlorate, hydrobromate, sulphate, hydrogen sulphate, dihydrogen phosphate, citrate, maleate, tartrate, fumarate, gluconate, methanesulphonate, 2-naphtalenesulphonate, etc., and the addition salts which allow suitable separation or crystallization of the compounds of formula (I), such as picrate or oxalate, or the addition salts with optically active acids, for example camphorsulphonic acids and mandelic or substituted mandelic acids.

When the compounds of formula (I) have a free carboxyl group, the salts also comprise the salts with inorganic bases, preferably those with alkaline metals such as sodium or potassium, or with organic bases.

The optically pure stereoisomers, and also the mixtures of isomers of the compounds of formula (I), due to the asymmetric carbon, in any proportion, are also part of the present invention.

More particularly compounds of formula (I) are the compounds in which the configuration of the carbon of the propanolamine bearing the OH group is (S).

The compounds of formula (I) may be in the form of "cis" or "trans" geometrical isomers, depending on the relative position of the substituents in positions 1 and 4 of the cyclohexyl ring (marked with a star). These pure isomers and their mixtures, in any proportion, are part of the present invention.

The mixtures of optical and geometrical stereoisomers above, in any proportion, are also part of the present invention.

The process of preparation of the compounds of formula (I) is disclosed in WO 02/44139.

The compounds of formula (I) are useful for the preparation of medicaments suitable to prevent and/or treat, in female patients in need thereof, diseases and/or disorders related to pregnancy related tissues apoptosis related, such as sexual cycle disorders, fertility disorders and pregnancy disorders, as well as preterm premature rupture of fetal membranes, as well as preterm labor, in particular preterm labor triggered by genital tract infection. Such patients can be readily identified by the routine analysis.

The expression "female mammalian patients" used herein refers in particular to women.

The expression "sexual cycle disorders" used herein refers to disorders of the female menstrual cycle, in particular those associated with impaired uterine apoptosis, as suggested by Qian Zhang et al., Endocrinology 147(5), 2215-2227, 2006

The expression "fertility disorders" used herein refers to disorders of the female fertility, in particular those associated with impaired uterine apoptosis, such as implantation as disclosed by Schlafke et al., *Anat. Rec.* 212:47-56, 1985; Parr et al., *Biol. Reprod.* 36:211-225, 1987; Welsh et al., *Am. J. Anat.* 192:215-231, 1991 and Joswig et al., *Reproductive Biology and Endocrinology* 1:44, 2003.

The expression "pregnancy disorders" used herein refers to disorders of the pregnancy in female mammalian, in particular those associated with impaired uterine apoptosis, such as early pregnancy as as disclosed by Schlafke et al., *Anat. Rec.* 212:47-56, 1985; Parr et al., *Biol. Reprod.* 36:211-225, 1987; Welsh et al., *Am. J. Anat.* 192:215-231, 1991 and Joswig et al., *Reproductive Biology and Endocrinology* 1:44, 2003.

For the uses of the invention, an effective amount of a compound of formula (I), or of a pharmaceutically acceptable salt thereof, is administered to the mammals which require such a treatment.

The compounds of formula (I) above, and the pharmaceutically acceptable salts thereof, may be used at daily doses of 0.01 to 20 mg per kilo of body weight of the mammal to be treated, preferably at daily doses of from 0.1 to 10 mg/kg. In humans, the dose may vary preferably from 0.5 mg to 1500 mg per day, in particular from 2.5 to 500 mg, depending on the age of the individual to be treated, the type of treatment, prophylactic or curative, and the seriousness of the disorder. The compounds of formula (I) are generally administered as a dosage unit of 0.1 to 500 mg, preferably of 0.5 to 100 mg, of active principle, one to five times a day.

Said dosage units are preferably formulated in pharmaceutical compositions in which the active principle is mixed with a pharmaceutical excipient.

Thus, according to another of its aspects, the present invention relates to pharmaceutical compositions containing, as an active principle, a compound of formula (I) above or a pharmaceutically acceptable salt thereof.

In the pharmaceutical compositions of the present invention for oral, sublingual, subcutaneous, intramuscular, intravenous, topical, transdermal or rectal administration, the active ingredients of formula (I) above, and the pharmaceutically acceptable salts thereof, may be administered in unit administration forms, mixed with conventional pharmaceutical supports, to animals and humans for treating the above-mentioned disorders. The unit administration forms which are suitable comprise oral forms such as tablets, gel capsules, powders, granules and oral solutions or suspensions, sublingual and buccal administration forms, subcutaneous, intramuscular or intravenous administration forms, local administration forms and rectal administration forms.

When a solid composition in the form of tablets is prepared, the main active ingredient is mixed with a pharmaceutical vehicle such as gelatin, starch, lactose, magnesium stearate, talc, gum arabic or the like. The tablets may be coated with sucrose or other suitable materials, or they may be treated such that they have sustained or delayed activity and that they release, in a continuous manner, a predetermined amount of active principle.

A preparation of gel capsules is obtained by mixing the active ingredient with a diluent and pouring the mixture obtained into soft or hard gel capsules.

A preparation in the form of a syrup or elixir may contain the active ingredient together with a sweetener, preferably a calorie-free sweetener, methylparaben and propylparaben as antiseptics, and also a flavour enhancer and a suitable colorant.

The water-dispersible powders or granules may contain the active ingredient mixed with dispersing agents or wetting agents, or suspending agents, such as polyvinylpyrrolidone, and also with sweeteners or flavour correctors.

For local administration, the active principle is mixed into an excipient for preparing creams or ointments, or it is dissolved in a vehicle for intraocular administration, for example in the form of an eyewash.

For rectal administration, use is made of suppositories prepared with binders which melt at rectal temperature, for example cocoa butter or polyethylene glycols.

For parenteral administration, aqueous suspensions, saline solutions or injectable sterile solutions which contain pharmacologically compatible dispersion agents and/or wetting agents, for example propylene glycol or butylene glycol, are used.

The active principle may also be formulated in the form of microcapsules, optionally with one or more supports or additives.

Figure 1:
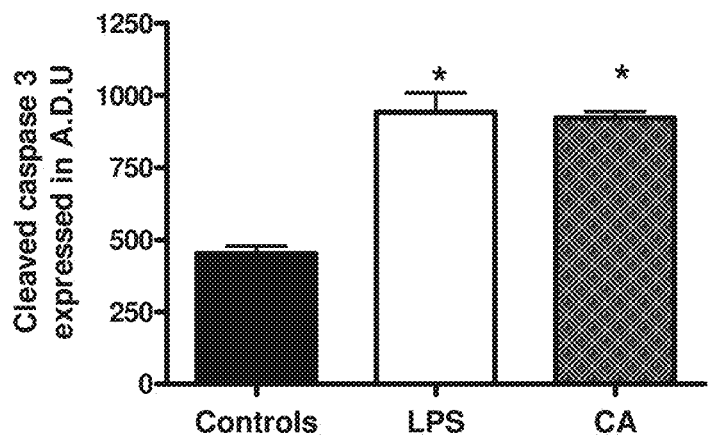
FIG. 1 represents Western Blot Analysis with semi-quantification showing the expression of cleaved caspase-3 protein. CTRL=control; LPS=10 µg/ml LPS, 48 h; CA=Chorioamnionitis. Experiments were performed in myometrial samples obtained from 3 different women with Chorioamnionitis (CA group), and with 5 myometrium, obtained at cesarean delivery from 5 different women with uncomplicated pregnancies and stimulated, or not, with LPS (LPS and CTRL groups respectively). *P<0.05 vs. controls.

The following examples further illustrate the present invention:

EXAMPLES

Drugs and Solutions

Lipopolysaccharide (LPS) (*Escherichia coli* 055:B5, ref: L2880) was purchased from Sigma-Aldrich and was dissolved in distilled water. Compound A was a gift from Sanofi-Midy Research Center, Exploratory Research Department, Sanofi-Aventis S.p.A. It was dissolved in a mixture of absolute ethanol 30%, dimethylsulfoxide 2%, and distilled water for the 1 mM solution and thereafter diluted in distilled water. The final maximal bath concentration was 0.3% for ethanol and 0.02% for DMSO.

Biological Samples

Myometrial biopsies were obtained from women during pregnancy in four different clinical situations as outlined: i) a woman with established chorioamnionitis undergoing postpartum hysterectomy; ii) a woman undergoing postpartum hysterectomy for postpartum hemorrhage in the absence of chorioamnionitis; iii) 3 women undergoing elective caesarean section with established chorioamnionitis; iv) 10 women undergoing elective caesarean section for other reasons (cephalo-pelvic disproportion) in the absence of chorioamnionitis. For women undergoing caesarean section, the procedures were all performed prior to the onset of labor at a gestation period between 38 and 40 weeks of pregnancy. Clinical chorioamnionitis was defined classically (Redline R W et al. Placenta 2005; 26 Suppl A: S114-117) as the presence of uterine tenderness and/or purulent or foul-smelling amniotic fluid with any 2 of the following: antepartum temperature of 37.8° C. or more, maternal tachycardia (more than 120 beats/min), maternal leukocytosis more than 18,000 cells/mm3, or fetal tachycardia (more than 160 beats/min) and was confirmed, in all cases included in the present study, by either a positive culture of the placenta or an histological assessment of the placenta by a single pathologist using validated criteria (Redline R W et al. Pediatr Dev Pathol 2003; 6: 435-448). Therefore in the rest of this study chorioamnionitis refers to confirmed chorioamnionitis.

Myometrial strips were excised from an immediately subserosal site where the majority of the fibers are in a longitudinal orientation, at an antiplacental site, as previously described (Rouget C, et al. J Clin Endocrinol Metab 2005; 90: 1644-1650, Leroy M J, et al. Biochem Pharmacol 1989; 38: 9-15). This study was approved by the "Comité Consultatif de Protection des Personnes pour la Recherche Biomédicale" (CCP-PRB, Dijon, France) and informed consent was obtained from all donors.

Tissues obtained from women with confirmed chorioamnionitis or postpartum hemorrhage, were either used fresh to perform western blot experiments, or embedded in paraffin for histological assessment and Hoechst staining, as described below.

Myometrial biopsies obtained from uncomplicated pregnancies were used to develop the LPS experimental model mimicking the effects of chorioamnionitis.

Stimulation of Myometrial Biopsies by *E. Coli* LPS

Myometrial biopsies obtained from women with uncomplicated pregnancies were immediately transferred in sterile Dubelcco's Modified Eagle Medium (DMEM) and washed twice with sterile Phosphate Buffer Saline (PBS). Biopsies were cut into small strips, each being placed in a 24-well plate containing 2 ml of culture medium DMEM, without the use of antibiotics. Strips were then incubated at 37° C. with 5% $CO_2$ for 48 h in order to allow cytokine levels to return to basal values (Fortunato S J, et al. Am J Reprod Immunol 1994; 32: 184-187).

In order to reproduce with LPS (*Escherichia coli* 055:B5) the findings on myometrial samples obtained from women with chorioamnionitis, myometrial strips were incubated with three different concentrations of LPS (50 ng/ml, 1 µg/ml and 10 µg/ml) at three different times (8 h, 24 h, 48 h).

In a second set of experiments, in order to assess the role of TNF in LPS-induced apoptosis in myometrial tissue, the strips were incubated with LPS 10 μg/ml for 48 h with or without anti TNF antibodies (0.6 μg/ml) (Human TNF alpha/TNFSF1A antibody, R&D systems Europe, Lille, France, the concentration of the antibody used was chosen based on the manufacturer's recommendations).

In a third set of experiments aimed to assess the ability of ADRB3 stimulation to oppose LPS-induced apoptosis, myometrial strips were incubated with LPS 10 μg/ml for 48 h in the presence or absence of Compound A, a selective ADRB3 agonist (Croci T et Al. J Pharmacol Exp Ther 2007; 321: 1118-1126) (0.1 μM, 1 μM, and 10 μM) added immediately prior to begin LPS stimulation. Time-matched control experiments were performed with the solvent of Compound A, i.e. distilled water containing ethanol 0.3% and DMSO 0.02% as final bath concentration, both non-stimulated and LPS-stimulated myometrial samples.

At the end of the stimulation period, the supernatants samples and tissues were quickly frozen in liquid nitrogen and stored at −80° C.

Western Blotting Analysis

Snap-frozen myometrial tissues were homogenized with Ultra-Turrax in homogenization buffer [10 mM Tris-HCl (pH 7.4), 1 mM EDTA, 40 mg/ml$^{-1}$ leupeptine, 2 mM Pefabloc]. After an initial centrifugation at 500×g for 15 min at 4° C., total protein supernatant content was determined by the Bradford method with BSA as standard. Samples (40 μg of protein by lane) were dissolved (vol/vol) in 2× Laemmli buffer (Laemmli U K et al. J Mol Biol 1970; 47: 69-85) and boiled for 5 min before electrophoresis on a 10% SDS-PAGE. Proteins were transferred to a nitrocellulose membrane (Hybond-P, Amersham Biosciences). In order to block non specific antibody binding, membranes were incubated for 1 h in 10% nonfat dried milk powder in Tris-buffered saline/Tween 20 (TBST) (10 mM Tris, 150 mM NaCl, and 0.1% Tween 20, pH 7.8) at room temperature. Blocked membranes were washed 3 times with TBST. The blots were then incubated overnight at 4° C. with a 1:200 dilution of primary cleaved caspase-3 antibody (ASP175, Cell Signaling Technologies, Beverly, Mass., USA) or a 1:500 dilution of primary BAX polyclonal antibody (sc-493, Santa Cruz, USA) or a 1:500 dilution of primary BCL2 polyclonal antibody (sc-7382, Santa Cruz, USA) in 1% non fat dried milk powder in PBST. After three washes with PBST, the blots were incubated for 45 min with horseradish peroxidase-conjugated antirabbit IgG (NA 934, Amersham, USA) or antimouse IgG (NA 931, Amersham, USA) whole antibody at a dilution of 1:10000 at room temperature and thereafter washed five times with PBST. Immunoreactive proteins were detected by chemiluminescence (ECL™ detection reagents, RPN2105, Amersham, USA) and exposure to a X-ray film (Hyperfilm™, Amersham Bioscience, USA). The intensities of the bands were analyzed densitometrically using the NIH Image 1.62 program and normalized with intensity of bands obtained with monoclonal antibody to Glyceraldehyde 3-Phosphate Dehydrogenase (GAPDH) used as protein loading control. Results are expressed as the mean±s.e.m. in Arbitrary Density Unit (A.D.U).

Immunohistochemical Analysis

The myometrial strips were fixed for 1 h with paraformaldehyde 4%, then embedded in paraffin and cut into 5-micrometer-thick sections. After deparaffinization of myometrial sections, and rehydratation, antigen retrieval was performed by incubating slides 10 min in warm citric acid buffer pH 6 with a pressure cooker. After endogenous peroxidase activity was blocked with hydrogen peroxide ($H_2O_2$) 3%, slides were incubated either with primary anti-cleaved caspase-3 IgG (1:100), washed three times with phosphate buffered saline (PBS) and then incubated with biotinylated anti-rabbit (1:600) immunoglobulin respectively for 1 h. After a new washing, slides were incubated in peroxidase labelled streptavidin (1:800) for 30 min and then with 3-amino-9-ethyl carbazole (AEC) solution until a clearly visible color was developed. The reaction was stopped by extensive washing in double distilled water. Subsequently, the preparations were counterstained with hematoxilin. The histological changes were evaluated in term of variation of global intensity of staining. Negative controls were carried out by omitting the primary antibody.

Hoechst Staining

To distinguish between apoptotic and necrotic cells, chromatin condensation state was assessed by staining of nuclei with Hoechst-33342. Paraffin embedded sections of myometrium samples were re-hydrated as described above. Slides were then incubated for 2 min with Hoechst-33342 (2 μg/ml). The slides were rinsed with distilled water and mounted with Aquatex©. The stained nuclei were visualized with convert fluorescent microscope at a magnification of ×100, using excitation light at 350 nm.

Real Time Quantitative RT-PCR

Total RNA was prepared from 5 myometrial tissues obtained from 5 different women, using Trizol solution (Life Technologies, Groningen, The Netherlands) according to the manufacturer's instructions. The integrity of RNA was verified by edithidium bromide staining of agarose gel analysis and by an optical density (OD) absorption ratio OD260 nm/OD280 nm≥1.8. One microgram of total RNA was reverse transcribed with Super script II RNAase H-reverse transcriptase (Invitrogen Life Technologies, Groningen, The Netherlands) using oligo (dT) according to the manufacturer's instruction. Real time quantitative PCR analyses were performed using 25 ng of reverse transcribed total RNA with 200 nM of both sense and anti sense primers in a final volume of 25 μl using the SYBR Green PCR jumpstart reagent (Sigma, Saint Louis, Mo., USA) in an iCycler iQ real time detection system instrument (Bio-Rad, Marnes-la-Coquette, France). PCR products were also analyzed on edithium bromide stained agarose gel to ensure that a single amplicon of the expected size was indeed obtained.

Each reaction was performed in duplicate and Glyceraldehyde-3-phosphate dehydrogenase (GAPDH) was used in each experiment to control for variability in the quantities of cDNA. Relative quantification for any given gene, expressed as fold variation over control, was calculated after determination of the difference between cycle threshold (Ct) value of the given gene according to manufacturers protocol using the formula $2^{-\Delta(\Delta CtA - \Delta CtB)}$, in which ΔCtA is ΔCt of the gene of interest; ΔCtB is ΔCt of GAPDH. ΔCt=Ct of the experimental group—Ct of the control group. PCR was performed using specific primers: GAPDH (Forward, 5'TGCACCAC-CAACTGCTTAGC3' (SEQ ID NO:1), and Reverse, 5'GGCATGGACTGTGGTC-ATGAG3' (SEQ ID NO:2)) and CASPASE-3 (Forward, 5' AGAACTGGACTGTG-GCATTGAG 3' (SEQ ID NO:3), and Reverse, 5' GCT-TGTCGGCATACTGTTTCAG 3' (SEQ ID NO:4)).

Cytokines Level Measurement

Cytokines measurements were determined by Cytometric Bead Array (CBA; Bender MedSystems). Supernatants of 5 myometrial strips were incubated with labeled capture beads and detection reagent for 3 h in the dark at room temperature, and analyzed with a flow cytometer (FACSCalibur; BD Biosciences) by using the respective CBA Analysis software (BD Biosciences) and Bender MedSystems software. Cytokine standards for quantification (pg/mL) as well as the blanks were handled in the same manner as the samples. Each experiment was performed in duplicate to ensure for reproducibility of results.

Statistical Analysis of Results

Differences among groups were determined by analysis of variance (ANOVA) followed by the Dunn's multiple comparison test. Statistical analysis was carried out using GraphPad Instat version 3 (GraphPad Software, San Diego, Calif.). All differences were considered significant when P<0.05.

Effect of the Selective ADRB3 Agonist Compound A on Apoptosis and Inflammation

Immunostaining of 4 myometrial tissues samples obtained from 4 different women with confirmed chorioamnionitis, using cleaved caspase-3 antibody, showed an intense staining (data not shown) that was observed neither in one control tissue obtained from a woman with postpartum hemorrhage (Sheiner E et al. J Matern Fetal Neonatal Med 2005; 18: 149-154) (data not shown) nor in 3 tissues obtained at elective cesarean delivery (data not shown). This staining was specifically located in myometrial cells. LPS stimulation in optimal conditions (i.e 10 µg/ml for 48 h, determined after time course—8 h, 24 h, 48 h—and dose response—50 ng/ml, 1 µg/ml, 10 µg/ml—experiments of LPS stimulation), was also associated with an intense cleaved caspase-3 staining specifically located in myometrial cells (data not shown).

Hoechst-33342 staining of myometrial section obtained from women with chorioamnionitis (n=4), postpartum hemorrhage (n=1) or elective cesarean delivery stimulated (n=4) or not (n=4) with LPS, showed that chorioamnionitis and LPS stimulation (data not shown), were both associated with an increased proportion of cells with condensed chromatin, indicating apoptosis initiation, compared with postpartum hemorrhage or cesarean delivery (data not shown).

Western blotting of membranes prepared from pregnant myometrium obtained from the same 3 women with chorioamnionitis or from 5 cesarean section and stimulated, or not (controls), with LPS, revealed a 17-kDa and a 19-kDa bands corresponding to cleaved caspase-3 (data not shown). Densitometric immunoblot analysis indicated that cleaved caspase-3 protein was significantly overexpressed both in case of chorioamnionitis and after LPS stimulation compared with elective cesarean delivery without LPS stimulation used as control (expressed in arbitrary density unit, ADU, 921±39, 941.6±134, vs 452±50.6, for chorioamnionitis, LPS 10 µg/ml and control group respectively, P<0.05) (FIG. 1). The overexpression of cleaved caspase-3 induced by LPS stimulation was in the same extent as that observed in western blot experiments performed in membranes prepared from pregnant myometrium women with chorioamnionitis (FIG. 1) providing external validation of in vitro LPS induced model of chorioamnionitis.

Figure 2:
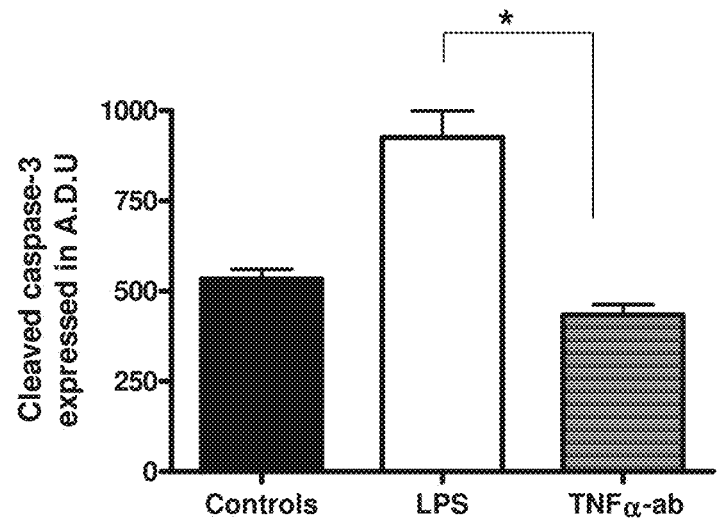
FIG. 2 illustrates Western Blot Analysis with semi-quantification showing the expression of cleaved caspase-3 protein. Controls=time-matched experiments; LPS=10 µg/ml LPS 48 h, TNFα-ab=10 µg/ml LPS+0.6 µg/ml TNFα-ab, 48 h. Experiments were performed on three myometrium obtained at elective cesarean delivery from three different women. *P<0.05 vs. LPS.

This over-expression of cleaved caspase-3 was strongly antagonized by the blockade of TNF-alpha receptor with a selective TNF-alpha antibody suggesting that LPS-induced apoptosis in human near-term myometrium involves TNF-alpha signaling pathway (FIG. 2, ANOVA P<0.05, n=3)
Our model of inflammation was validated by the measurement of supernatant cytokines production. In our experimental conditions, LPS stimulation was associated, at 48 h, with a significant increase of IL6 (mean±sem in pg/ml 28860±5257 vs 61860±12190, for control and LPS groups respectively; n=10 experiments from 5 different women, P<0.05) and IL8 (in pg/ml 8855±1486 vs. 16080±2834, for control and LPS groups respectively; n=10 experiments from 5 different women, P<0.05) but not IL1B, IL10, IL12B or TNF levels.

This over expression of cleaved caspase-3 protein was also observed at a transcriptional level since quantitative real-time RT-PCR showed that, compared with time matched controls, incubation with 10 µg/ml LPS for 48 hours was associated with a 2.36±0.22 fold increased in transcript levels (n=3 experiments performed with myometrial tissues obtained from 3 different women).

This weak effect on caspase-3 mRNA expression might be explained by our experimental conditions, i.e. 48 hours of incubation with LPS. Indeed, in an exploratory analysis we assessed time-trend for caspase-3 mRNA expression (3, 6, 12, 48 and 72 hours) and found that the peak for mRNA expression occurred around 3 hours of stimulation (in fold increase compared with controls: 8.6, 6.1, 2.3, 2.1, 1.2 at 3 h, 6 h, 16 h, 48 h and 72 h respectively).

Figure 3:
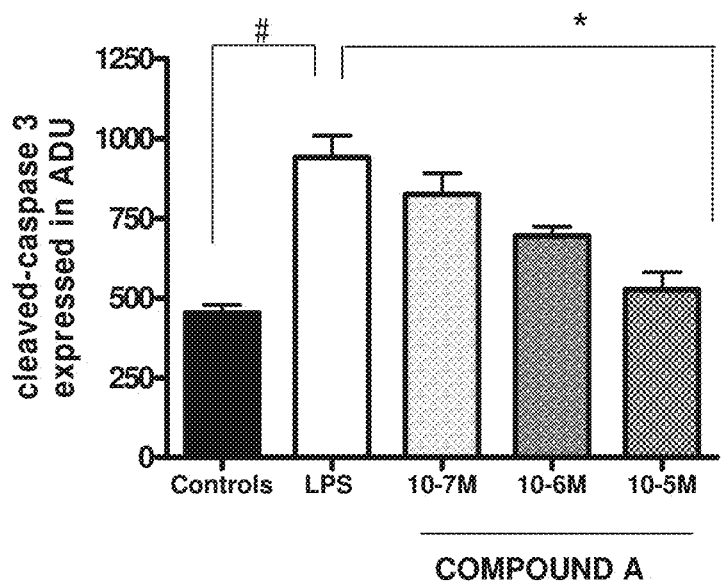
FIG. 3 illustrates Western Blot Analysis with semi-quantification showing the expression of cleaved caspase-3 protein. Controls=time-matched experiments; LPS=10 µg/ml LPS 48 h. Compound A ($10^{-7}$M, $10^{-6}$M, $10^{-5}$M) was added 20 min. prior to LPS stimulation. Experiments were performed on five myometrium, obtained at elective cesarean delivery from five different women. #P<0.05 vs controls, *P<0.05 vs. LPS.
Figure 4:
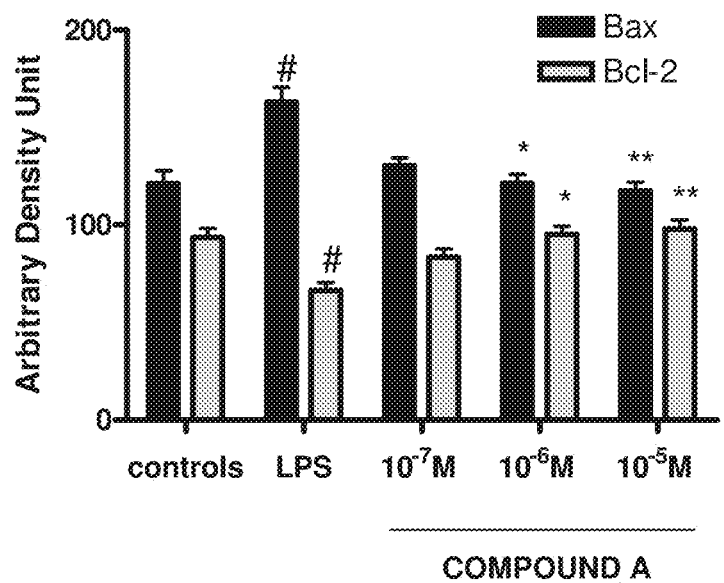
FIG. 4 illustrates Western Blot Analysis with semi-quantification showing the expression of BAX and Bcl-2 protein. Controls=time-matched experiments; LPS=10 µg/ml LPS 48 h. Compound A ($10^{-7}$M, $10^{-6}$M, $10^{-5}$M) was added 20 min. prior to LPS stimulation. Experiments were performed on seven myometrium, obtained at elective cesarean delivery, from seven different women. #P<0.05 vs controls, *P<0.05 vs. LPS, **P<0.01 vs LPS.

In a further set of experiments, western blot experiments revealed that the selective ADRB3 agonist, Compound A, was able to significantly antagonize LPS-induced changes in cleaved caspase-3 expression in a concentration dependent manner (FIG. 3, ANOVA P<0.001,). Furthermore, we observed that LPS-induced activation of the mitochondrial pathway of apoptosis, as expressed by BAX and BCL2 protein up- and down-regulation, respectively, was antagonized in a concentration dependant manner (FIG. 4, ANOVA, P<0.01). Compound A had no effect by itself on cleaved caspase-3, BAX and BCL2 expression in tissues not stimulated with LPS (data not shown). The solvent for the highest concentration of Compound A, i.e. distilled water containing ethanol 0.3% and DMSO 0.02%, had no effect on cleaved caspase-3, BAX and BCL2 expression in tissues either not stimulated or stimulated with LPS (data not shown).

The effect of Compound A on caspase-3 over-expression was, at least partially, explained at a transcriptional level since quantitative real-time RT-PCR, showed that ADRB3 treatment was associated with a decreased level of caspase-3 transcripts (in fold increase, normalized to GAPDH, compared with controls 2.08±0.63, 1.17±0.81, 0.84±0.53, 0.93±0.41, respectively for LPS alone and with Compound A $10^{-7}$, $10^{-6}$ and $10^{-5}$ M respectively, ANOVA, P<0.05).

Figure 5A:
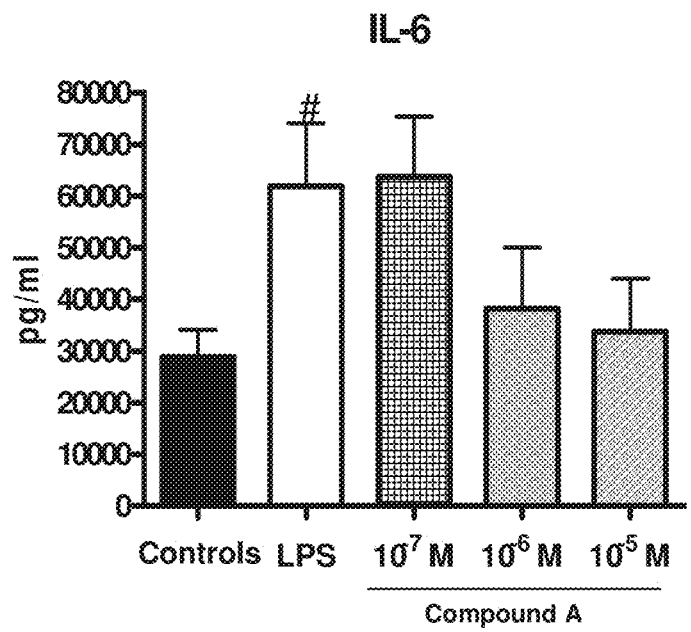
FIGS. 5A and 5B show the effect of Compound A on the concentrations of IL-6 and IL-8, respectively. Results (mean±s.e.m, in pg/ml) are from five experiments performed in duplicate in myometrium, obtained at elective cesarean delivery, from five different women. #P<0.05 vs controls, *P<0.05 vs LPS, **P<0.01 vs LPS.
Figure 5B:
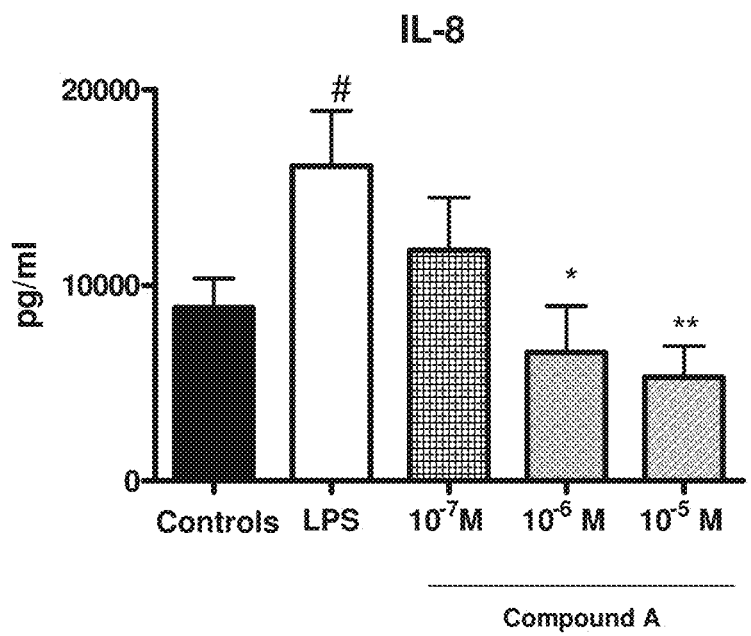

Finally, Compound A decreased IL6 and IL8 in a concentration dependent manner, even though the effect was statically significant only for IL8 (ANOVA P=0.01; FIG. 5). Compound A had not effect by itself on IL6 and IL8 release in tissues not stimulated with LPS (data not shown). TNF was under the lower level of detection for the flow-cytometry technique at 48 hours.

Altogether, these results demonstrate that Compound A reverses an LPS-induced apoptosis and cytokines production in human near term myometrium.

Pharmaceutical Composition According to the Invention

As a representative example, a unitary dosage form of a compound of the invention in the form of a tablet may comprise the following constituents:

| | |
|---|---|
| Compound A | 50.0 mg |
| Mannitol | 223.75 mg |
| Sodium Croscaramellose | 6.0 mg |
| Corn starch | 15.0 mg |
| Hydroxypropyl-methylcellulose | 2.25 mg |
| Magnesium stearate | 3.0 mg |

The invention claimed is:

1. A method of reducing the risk of pre-term labor in a pregnant female patient having increased uterine apoptosis comprising:

(a) determining that said pregnant female patient has increased uterine apoptosis, said risk of pre-term labor in the pregnant female patient being increased as a result of said increased uterine apoptosis; and (b) administering to said pregnant female patient having increased uterine apoptosis a therapeutically effective amount of a beta-3 adrenergic receptor agonist compound of formula (I):

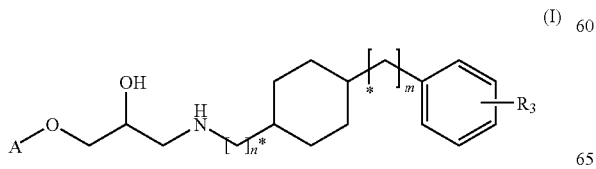

wherein:

A is a group of formula (a) or (b):

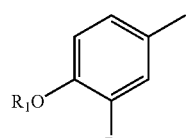

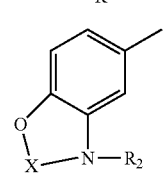

where:

R represents a hydrogen or halogen atom, an —S(O)z(C$_1$—C)alkyl group, an —NHSO$_2$(C$_1$-C$_4$)alkyl group, an —SO$_2$NH(C$_1$-C$_4$)alkyl group, an —NHSO$_2$phenyl-(C$_1$-C$_4$)alkyl group or an —NHSO$_2$phenyl group, said phenyl possibly being substituted with a halogen atom, with a (C$_1$-C$_4$)alkyl group or with a (C$_1$-C$_4$)alkoxy group;

R$_1$ represents a hydrogen atom or a (C$_1$-C$_4$)alkyl group, a —CO(C$_1$-C$_4$)alkyl group, a phenyl-(C$_1$-C$_4$)alkyl group or a —CO-phenyl group, said phenyl possibly being substituted with a halogen atom or with a $(C_1-C_4)$alkoxy group;

$R_2$ is a hydrogen atom, an —$SO_2(C_1-C_4)$alkyl group, an —$SO_2$phenyl-$(C_1-C_4)$alkyl group or an —$SO_2$phenyl group;

X completes a ring of 5 to 8 atoms, said ring being saturated or unsaturated, possibly being substituted with one or two $(C_1-C_4)$alkyl groups and bearing one or two carbonyl groups;

n, m and z are, independently, 0, 1 or 2;

$R_3$ represents a hydrogen or halogen atom, a $(C_1-C_6)$alkyl group, a $(C_1-C_4)$alkoxy group, a —$COO(C_1-C_4)$alkyl group, a —$CO(C_1-C_4)$alkyl group, an —$NHSO_2(C_1-C_4)$alkyl group, an —$NHSO_2$phenyl-$(C_1-C_4)$alkyl group, —$NO_2$, —CN, —$CONR_4R_5$, —COOH, or a 4,5-dihydro-1,3-oxazol-2-yl or 4,4-dimethyl-4,5-dihydro-1,3-oxazol-2-yl group; and $R_4$ and $R_5$ represent, independently, a hydrogen atom, a phenyl, a $(C_1-C_4)$alkyl group or a phenyl-$(C_1-C_4)$alkyl group; or $R_4$ and $R_5$ with the nitrogen atom to which they are attached, may form a ring of 5 to 7 atoms;

or a stereoisomer or mixture of stereoisomers of said beta-3 adrenergic receptor agonist compound;

or a pharmaceutically acceptable salt of said beta-3 adrenergic receptor agonist compound or of said stereoisomer or mixture of stereoisomers thereof.

2. The method according to claim 1, wherein the patient having increased risk of preterm labor has chorioamnionitis.

3. The method according to claim 1, wherein the patient having increased risk of preterm labor has intrauterine growth restriction or preeclampsia.

4. The method according to claim 1, wherein the patient having an increased risk of preterm labor has premature rupture of fetal membrane.

5. The method according to claim 1, wherein n and m are each zero.

6. The method according to claim 1, wherein $R_1$ is a hydrogen atom.

7. The method according to claim 1, wherein R is chosen from an —$NHSO_2(C_1-C_4)$alkyl group, an —$NHSO_2$phenyl-$(C_1-C_4)$alkyl group or an —$NHSO_2$phenyl group.

8. The method according to claim 1, wherein $R_3$ is —COO$(C_1-C_4)$alkyl or —CO$(C_1-C_4)$alkyl or $CONR_4R_5$.

9. The method according to claim 1, wherein $R_3$ is in position 4 of the benzene.

10. The method according to claim 1, wherein z is 2.

11. The method according to claim 1, wherein X is methylene, ethylene or propylene.

12. The method according to claim 1, wherein X is a carbonyl, a —CO—CO-group, a —CO—C$((C_1-C_4)$alkyl$)_2$-CO-group, a methylene mono-substituted or disubstituted with $(C_1-C_4)$alkyl or a —$COCH_2$— group.

* * * * *

UNITED STATES PATENT AND TRADEMARK OFFICE
CERTIFICATE OF CORRECTION

PATENT NO. : 9,161,925 B2
APPLICATION NO. : 12/652317
DATED : October 20, 2015
INVENTOR(S) : Bardou It is certified that error appears in the above-identified patent and that said Letters Patent is hereby corrected as shown below:

On the Title Page:

Item [75] replace "Dijion" with --Dijon--;

Item [56] line 19 replace "pp. 518-513" with --pp. 516-518--; and line 21 replace "Katooka" with --Kataoka--.

In the Claims:

Column 14, claim 1, line 59-60: replace "-S(O)z($C_1$-C)alkyl group" with -- -S(O)z($C_1$-$C_4$)alkyl group--.

Signed and Sealed this
Twenty-first Day of June, 2016

Michelle K. Lee
*Director of the United States Patent and Trademark Office*